(12) United States Patent
Harper (10) Patent No.: US 7,102,751 B2
(45) Date of Patent: Sep. 5, 2006

(54) LASER-BASED SPECTROSCOPIC DETECTION TECHNIQUES

(75) Inventor: Warren W. Harper, Benton City, WA (US)

(73) Assignee: Battelle Memorial Institute, Richland, WA (US)

( * ) Notice: Subject to any disclaimer, the term of this patent is extended or adjusted under 35 U.S.C. 154(b) by 145 days.

(21) Appl. No.: 10/938,967

(22) Filed: Sep. 10, 2004

(65) Prior Publication Data

US 2005/0099632 A1 May 12, 2005

Related U.S. Application Data

(60) Provisional application No. 60/518,860, filed on Nov. 11, 2003.

(51) Int. Cl.
G01N 21/00 (2006.01)
(52) U.S. Cl. ...................................... 356/437
(58) Field of Classification Search ............... None
See application file for complete search history.

(56) References Cited

U.S. PATENT DOCUMENTS

| | | | |
|---|---|---|---|
| 4,509,130 A | 4/1985 | Menzies et al. | |
| 4,590,597 A | 5/1986 | Long-sheng et al. | |
| 4,594,511 A | 6/1986 | Cooper et al. | |
| 4,684,258 A | 8/1987 | Webster | |
| 4,856,899 A | 8/1989 | Iwaoka et al. | |
| 4,937,448 A | 6/1990 | Mantz et al. | |
| 5,202,560 A | 4/1993 | Koch et al. | |
| 5,301,014 A * | 4/1994 | Koch ......................... | 356/437 |
| 5,408,327 A | 4/1995 | Geiler et al. | |
| 5,416,582 A | 5/1995 | Knutson et al. | |
| 5,441,054 A | 8/1995 | Tsuchiya | |
| 5,636,035 A * | 6/1997 | Whittaker et al. .......... | 356/437 |
| 5,640,245 A | 6/1997 | Zybin et al. | |
| 5,737,077 A | 4/1998 | Lee et al. | |
| 5,815,277 A | 9/1998 | Zare et al. | |
| 5,969,825 A | 10/1999 | Bomse et al. | |
| 6,351,309 B1 | 2/2002 | Bomse et al. | |
| 6,353,476 B1 * | 3/2002 | Allen et al. ................. | 356/301 |
| 6,356,350 B1 | 3/2002 | Silver et al. | |

FOREIGN PATENT DOCUMENTS

| | | |
|---|---|---|
| EP | 0 373 945 B1 | 2/1994 |
| EP | 0 720 313 B1 | 6/1999 |
| EP | 0 995 984 A1 | 4/2000 |
| EP | 0995984 A1 | 4/2000 |

OTHER PUBLICATIONS

*Residual amplitude modulation in laser electro-optical phase modulation*, Whittaker, Gehrtz, Bjorklund, J. Opt. Soc. Am. B, vol. 2, No. 8, pp. 1320-1326 (Aug. 1985).

(Continued)

*Primary Examiner*—Gregory J. Toatley, Jr.
*Assistant Examiner*—Ali Allawi
(74) *Attorney, Agent, or Firm*—Klarquist Sparkman, LLP (57) ABSTRACT

One embodiment of the present invention includes: a modulated laser light source to transmit an interrogation light beam to a region including a substance for spectroscopic evaluation, a detector responsive to modulated light from the region to provide a corresponding modulated signal, and a signal processing subsystem responsive to the modulated signal to generate a spectroscopic absorption peak representation. This subsystem also estimates absorbance based on a derivative form of an absorption peak and a residual amplitude modulation level corresponding to the absorption peak.

27 Claims, 8 Drawing Sheets

OTHER PUBLICATIONS

*Analysis of Cleaved Coupled-Cavity ($C^3$) Diode Lasers-Part II: Frequency Modulation, Above Threshold Operation, and Residual Amplitude Modulation*, Streifer, Yevick, Paoli and Burnham, IEEE Journal of Quantum Electronics vol. QE-21, No. 6, pp. 539-550 (Jun. 1985).

*Frequency-modulation spectroscopy for trace species detection: theory and comparison among experimental methods*, Joel A. Silver, Applied Optics, vol. 31, No. 6, pp. 707-717 (Feb. 20, 1992).

Disselkamp et al., "Signal-to-noise enhancement techniques for quantum cascade absorption spectrometers employing optimal filtering and other approaches," Appl. Phys. B, 75:359-366 (2002).

Hjelme et al., "Optical interference fringe reduction in frequency-modulation spectroscopy experiments," Optics Letters, 20:1731-1733 (1995).

Edwards et al., "A diode laser based gas monitor suitable for measurement of trace gas exchange using micrometeorological techniques," Agriculture and Forest Meteorology, 115:71-89 (2003).

Mielke et al., "Reduction of Mode Partition Noise in a Multiwavelength Semiconductor Laser through Hybrid Modelocking," Technical Digest, IEEE, 1:348-349 (2002).

Wu et al., "Reduction of Fringe Noise in Wavelength Modulation Spectroscopy Using a One-Dimensional Focal Plane Array," Optical Review, 9:189-192 (2002).

Wu et al., "Efficient Reduction of Fringe Noise in Trace Gas Detection with Diode Laser Multipass Absorption Spectroscopy," Jpn. J. of Appl. Phys., 39:4034-4040 (2000).

Wu et al., "Quantitative Analysis of Trace Moisture in $N_2$ and $NH_3$ Gases with Dual-Cell Near-Infrared Diode Laser Absorption Spectroscopy," Anal. Chem., 70:3315-3321 (1998).

Coffer et al., "Collisional dephasing and the reduction of laser phase-noise to amplitude-noise conversion in a resonant atomic vapor," Physical Review A, 65:1-9 (2002).

Camparo, "Reduction of Laser Phase-Noise to Amplitude-Noise Conversion in the Gas-Cell Atomic Clock," 2002 IEEE International Frequency Control Symposium and PDA Exhibition, pp. 476-479 (2002).

Modugno et al., "Fundamental noise sources in a high-sensitivity two-tone frequency modulation spectrometer and detection of $CO_2$ at 1.6 mu m and 2 mu m," Appl. Phys. B, 67:289-296 (1998).

Burt et al., "Signal-to-noise enhancement in optical spectroscopy of single indium ions using amplitude modulation and synchronous detection," Rev. Sci. Instrum., 68:1348-1349 (1997).

Armerding et al., "Multipass optical absorption spectroscopy: a fast-scanning laser spectrometer for the *in situ* determination of atmospheric trace-gas components, in particular OH," Applied Optics, 35:4206-4219 (1996).

Sonnenfroh et al., "Ultrasensitive, visible tunable diode laser detection of $NO_2$," Applied Optics, 35:4053-4058 (1996).

Riris et al., "Signal-to-noise ratio enhancement in frequency-modulation spectrometers by digital signal-processing," Optics Letters, 19:144-146 (1994).

Shevy et al., "Linewidth reduction and frequency stabilization of a semiconductor laser with a combination of FM sideband locking and optical feedback," Optics Letters, 18:1071-1073 (1993).

Worsnop et al., "Chemical kinetic studies of atmospheric reactions using tunable diode laser spectroscopy," SPIE—Optical Methods in Atmospheric Chemistry, 1715:18-33 (1992).

Iseki et al., "A portable remote methane sensor using a tunable diode laser," Meas. Sci. Technol.,11:594-602 (2000).

Martini et al., "High-speed digital data transmission using mid-infrared quantum cascade lasers," Electr. Lett., 37:1290-1291 (2001).

Menyuk et al., "Temporal correlation measurements of pulsed dual $CO_2$ lidar returns," Opt. Lett., 6:301-303 (1981).

* cited by examiner

LASER-BASED SPECTROSCOPIC DETECTION TECHNIQUES

CROSS-REFERENCE TO RELATED APPLICATONS

The present application claims the benefit of U.S. Provisional Patent Application No. 60/518,860 filed 11 Nov. 2003, which is hereby incorporated by reference in its entirety.

GOVERNMENT RIGHTS

This invention was made with Government support under Contract Number DE-AC0676RLO1831. The Government has certain rights in the invention.

BACKGROUND

The present application relates to laser-based spectroscopy, and more particularly, but not exclusively, relates to noise reduction and absorbance estimation for spectroscopy based on frequency modulation of a laser.

Various techniques for detecting extremely low concentrations of a substance of interest have been developed that involve Frequency Modulation (FM) of a laser beam. FM techniques include those described as Frequency Modulation Spectroscopy (FMS), wideband FM, Wavelength Modulation Spectroscopy (WMS), and the like; by Joel Silver in *Frequency-Modulation Spectroscopy for Trace Species Detection: Theory and Comparison Among Experimental Methods*, APPLIED OPTICS, vol. 31, No. 6, pp.707–717 (20 Feb. 1992), which is hereby incorporated by reference.

Regardless of the particular type, for these techniques the frequency-modulated laser beam is typically directed through an analyte that is characterized by spectral absorption and/or dispersion of the interrogating light. The returned light, an altered form of the interrogating light, is detected and evaluated to determine a certain spectroscopic characteristic of interest. Frequency modulation of laser light typically results in a coincidental amount of Amplitude Modulation (AM), so-called Residual Amplitude Modulation (RAM), due to nonideal behavior of the laser and/or other elements of the system. RAM is often regarded as undesirable because of limits it can impose on the sensitivity of FM techniques.

To enhance sensitivity of laser-based spectroscopic detection, a double beam approach has been implemented that uses a reference light beam to cancel noise present in the interrogating light beam. For this approach, carefully matched detectors and light beam paths are often needed, which can lead to considerable expense and complexity. Moreover, various remote sensing applications cannot practically incorporate multiple, long-range beams. In some remote sensing applications that may be particularly desired for homeland security, pollution control, and the like; a single beam system can suffer from noise induced by atmospheric turbulence, optical component vibration, and/or one or more other noise sources that likewise alter intensity of the laser beam. Such "intensity noise" can significantly effect sensitivity.

Accordingly, there is a need for further contributions in this area of technology.

SUMMARY

One embodiment of the present invention is a unique spectroscopic detection technique. Other embodiments include unique systems, devices, apparatus, and methods for FM laser-based spectroscopy.

A further embodiment of the present invention includes a technique to reduce signal noise due to atmospheric turbulence, mechanical vibration of one or more optical components, or the like as a function of residual amplitude modulation. This technique provides for the reduction of intensity noise in systems based on only a single light beam and detector, although it can also be applied to systems having two or more light beams and/or detectors.

In a further embodiment, a technique is provided for evaluating absorbance based a level of residual amplitude modulation associated with an absorption peak. This technique provides for the estimation of absorbance where measurements typically needed to determine absorbance are not readily available; however, this estimation approach can also be utilized even when one or more such measurements are available. In still other embodiments, these techniques are combined, or otherwise modified or extended together or separately.

Yet a further embodiment includes: transmitting a modulated laser beam to a substance, receiving modulated laser light from the substance, determining an FM signal constituent and an AM signal constituent of the modulated laser light, and reducing noise as a function of the FM signal constituent and the AM signal constituent. In one particular form, the function corresponds to a relative comparison between the FM signal constituent and the AM signal constituent, such as a ratio.

Still a further embodiment includes: transmitting a modulated laser beam to a substance, detecting frequency-modulated light from the substance, evaluating the frequency-modulated light to identify a spectral absorption peak of the substance, and calculating a value corresponding to absorbance of the substance as a function of residual amplitude modulation associated with the peak. Alternatively or additionally, intensity noise of the peak is reduced based on a frequency modulation signal constituent and a residual amplitude modulation signal constituent.

Another embodiment includes: a modulated laser light source to transmit an interrogation light beam to a region including a substance for spectroscopic evaluation, a detector responsive to modulated light from the region to provide a corresponding modulated signal, and a signal processing subsystem responsive to the modulated signal to generate a spectroscopic representation of the substance with light intensity noise reduced as a function of a frequency modulation constituent and a residual amplitude modulation constituent of the modulated signal.

In another embodiment, a device includes logic executable with a processing subsystem to evaluate a modulated signal corresponding to frequency modulated light returned by a substance undergoing spectroscopic interrogation, the logic being further executable to identify a spectral absorption peak of the substance from the modulated signal and calculate a value corresponding to absorbance of the substance as a function of a level of residual amplitude modulation for the absorption peak and one or more parameters corresponding to magnitude of the absorption peak.

For another embodiment, a device includes logic executable with a processing subsystem to evaluate a modulated signal corresponding to frequency modulated light returned by a substance undergoing spectroscopic interrogation, the logic being further executable to generate a spectroscopic representation with noise reduced as a function of a frequency modulation signal constituent and a residual amplitude modulation signal constituent.

Optionally, one or more of these embodiments can include a modulated laser beam that travels a distance of at least 1 kilometer through a spectroscopic evaluation region. This distance can be the accumulated travel of the beam over multiple segments due to reflection/deflection or may directly span such distance across the region. In one non-limiting example of a long-range, remote sensing application; the modulated laser beam directly spans the distance though the atmosphere and the noise source includes atmospheric turbulence. In one form preferred for a long-path interrogation application, the distance traveled by the interrogating light beam is at least 25 meters. In a more preferred form of this type of application, the distance traveled by the interrogating light beam is at least 1 kilometer. For an even more preferred form of this application, the distance is at least 2 kilometers.

Accordingly, one object of the present invention is to provide a unique spectroscopic detection technique.

Another object is to provide a unique system, method, device, or apparatus for FM laser-based spectroscopy.

Other objects, embodiments, forms, features, advantages, aspects and benefits of the present invention shall become apparent from the detailed description and drawings included herein.

DETAILED DESCRIPTION

While the present invention may be embodied in many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

One embodiment of the present invention includes a technique to reduce signal noise due to atmospheric turbulence, mechanical vibration of one or more optical components, or the like based on residual amplitude modulation. This technique provides for the reduction of certain types of noise in systems having only a single light beam and detector, although it can also be applied to systems having multiple light beams and/or detectors. In another embodiment, a technique is provided for evaluating absorbance based a level of residual amplitude modulation associated with an absorption peak. This technique provides for the estimation of absorbance where measurements typically needed to determine absorbance are not readily available, such as the input power of the interrogating light and/or the power absorbed from the interrogating light; however, the estimation can also be utilized even where one or more such measurements are known. In still other embodiments, these techniques are combined, or otherwise modified or extended together or separately.

Figure 1:
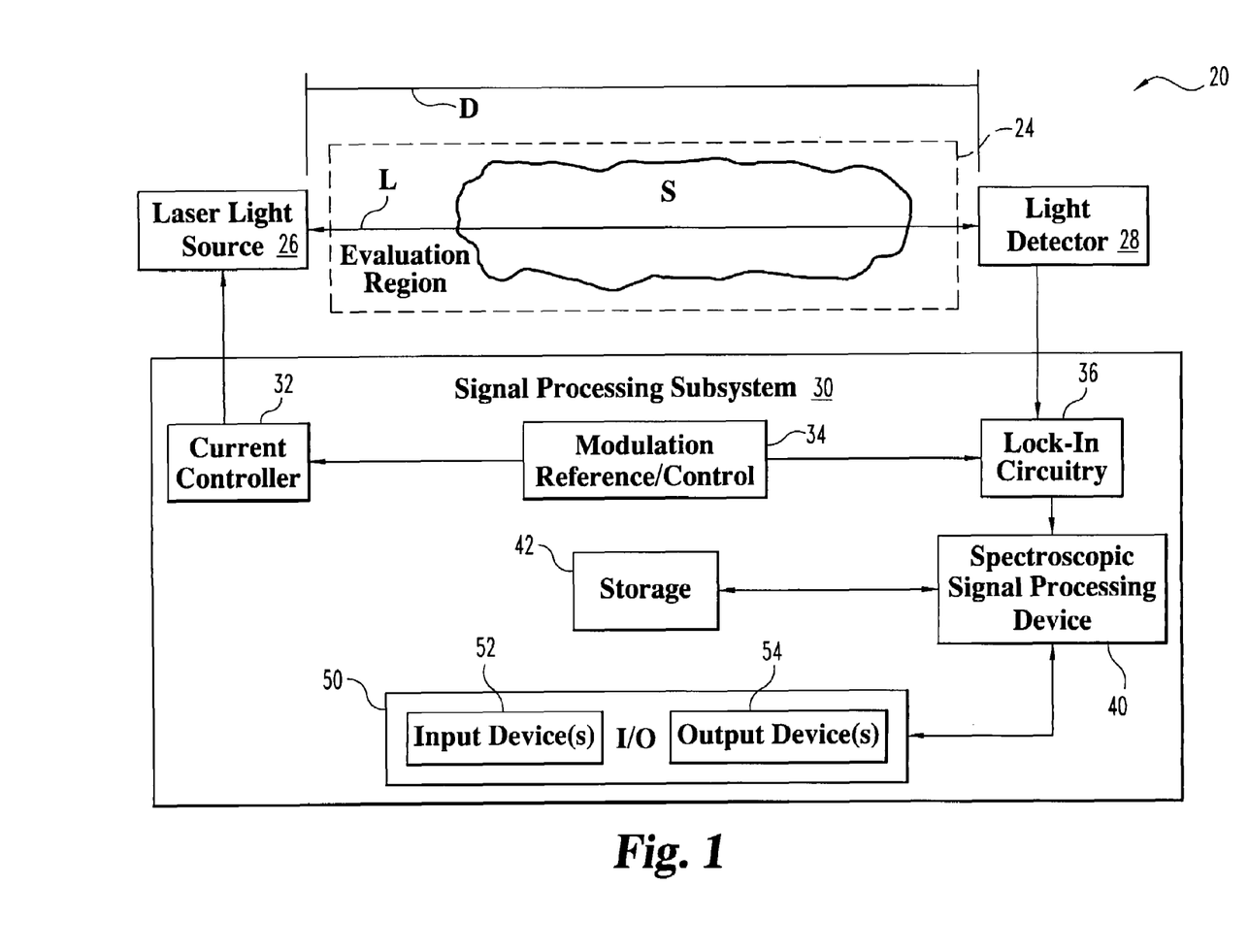
FIG. 1 is a schematic diagram of laser-based spectroscopy system.

For example, FIG. 1 depicts spectroscopic evaluation system 20. System 20 is operable to spectroscopically determine one or more attributes of substance S. Substance S is typically in a gaseous form within evaluation region 24. In one particular arrangement, region 24 corresponds to an outdoor area and substance S comprises the outdoor atmosphere in region 24. Such an arrangement may be directed to detection in the atmosphere of one or more chemical species indicative of a security threat, pollutants, or the like. System 20 further includes laser light source 26, light detector 28, and signal processing subsystem 30. Source 26 includes a laser of the current-controlled type such as a Quantum Cascade Laser (QCL) variety or other semiconductor diode variety. In other embodiments, a different type of laser can be utilized that has a desired wavelength ($\lambda$) output, a desired wavelength scan range and frequency modulation, and a desired degree of coherency and/or such other performance characteristics as are desired. For example, it is envisioned a lead-salt or gas-based laser type could be utilized in alternative embodiments.

Source 26 transmits a laser light beam L to region 24 to perform a spectroscopic interrogation of substance S. The returned response light is sensed with light detector 28. As represented FIG. 1, this output light beam L spans a distance D from source 26 to detector 28. Detector 28 is of a Mercury-Cadmium-Telluride (MCT) type, a photomultiplier tube type, a photodiode sensor type, or the like suitable to sense modulated light of desired character and provide a corresponding output signal. Light associated with region 24, source 26, and detector 28 can be conditioned, transmitted, or directed with optical fibers, reflectors, beam splitters, focusing and/or defocusing devices, isolators, modulators, and/or other optical components as desired to perform the techniques described herein.

Subsystem 30 is operatively coupled to source 26 and detector 28. Subsystem 30 includes current controller 32, frequency modulation reference/control 34, lock-in circuitry 36, spectroscopic signal processing device 40, data storage 42, and operator Input/Output (I/O) devices 50. Current controller 32 provides a regulated electrical current to source 26 to control the light output. In one aspect, this current is swept or scanned over a selected magnitude range to correspondingly change the wavelength of the light output over a selected wavelength scan range. This change typically takes the form of a triangle or ramp type of current waveform on a baseline current offset. The wavelength scan range can be selected to center on a spectral feature of a chemical species of interest, such as an absorption peak of a gas indicative of explosives.

In another aspect, the current output by controller 32 is frequency-modulated at a frequency typically much greater than the rate of change or sweep of the wavelength scan. This frequency modulation aspect is generated with controller 32 in response to a corresponding sinusoidal signal from frequency modulation reference/control 34. The instantaneous frequency, $\omega_i$, for this configuration is given as: $\omega_i=\omega_0+M\sin(\omega_m t)$, where: $\omega_0$ is the center frequency, M is the modulation index, and $\omega_m$ is the modulation frequency. Accordingly, laser light beam L from source 26 is transmitted in a frequency-modulated form to substance S in region 24. While this transmitted light has an intended degree of frequency modulation, there is also typically an inherent degree of residual amplitude modulation present.

Frequency modulation reference/control 34 also provides the frequency modulation waveform to lock-in circuitry 36 which is arranged to provide a frequency-modulation signal output representative of the input signal from detector 28. This frequency-modulation signal output provides a standard, derivative-type absorption waveform. In contrast to this derivative, FM signal format, the corresponding direct absorption waveform often has more signal noise and a significant baseline offset. This frequency-modulation signal can be adjusted to select a given harmonic of the modulation frequency for evaluation to further enhance signal-to-noise as appropriate. Lock-in circuitry 36 also provides a quadrature output corresponding to a signal 90 degrees out-of-phase with the synchronized frequency modulation signal output.

Modulated signals from lock-in circuitry 36 are sent to spectroscopic signal processing device 40. Device 40 can be comprised of one or more components of any type suitable to process the signals received from lock-in circuitry 36, including digital circuitry, analog circuitry, or a combination of both. When needed, device 40 includes appropriate interface/conversion circuitry to provide signal information in a desired format, such as an analog-to-digital converter to name just one example. A multiple component form of device 40 can be of an integrated, single-unit type or can be arranged with one or more components located remote from one or more other components. Device 40 can include one or more processors of a programmable type; a dedicated, hardwired state machine; or a combination of these. For a multiple processor form; distributed, pipelined, and/or parallel processing can be utilized as appropriate. A computer network of a Local Area Network (LAN), a Municipal Area Network (MAN), and/or a Wide Area Network (WAN) of either a private type or publicly accessible type, such as the internet can be coupled to subsystem 30 (not shown) and/or utilized to communicate between different portions of subsystem 30 (not shown).

Data storage 42 can be a memory of a solid-state variety, electromagnetic variety, optical variety, or a combination of these forms; and can be volatile, nonvolatile, or a mixture of these types. Storage 42 can include any of various portable/removable media, such as: a floppy disk, cartridge, or tape form of removable electromagnetic recording media; an optical disk, such as a CD or DVD; an electrically reprogrammable solid-state type of nonvolatile memory, and/or such different variety as would occur to those skilled in the art. Storage 42 can be at least partially integrated with device 40, or separate therefrom as one or more operatively coupled components.

Device 40 executes operating logic to perform various operations to be further described hereinafter. This logic can be in the form of software programming instructions, firmware, and/or of a hardwired form, just to name a few. Furthermore such logic can be in the form of one or more signals carried in storage device 42 and/or one or more parts of a computer network coupled to subsystem 30 (not shown). In one example, logic signals to perform one or more operations are transmitted to/from processor(s) of subsystem 30 through such a network. Alternatively or additionally, programming for subsystem 30 can be transported or disseminated through one or more portable/removable memory types that removably interfaces with subsystem 30 to become a component of storage 42.

Operator I/O devices 50 are also coupled to device 40, and include one or more operator input devices 52 and one or more operator output devices 54. Operator input devices 52 can include a keyboard, mouse or other pointing device, a voice recognition input subsystem, and/or a different arrangement as would occur to those skilled in the art. Operator output devices 54 can be of a Cathode Ray Tube (CRT) type, Liquid Crystal Display (LCD) type, plasma type, Organic Light Emitting Diode (OLED) type, printer, or such different type as would occur to those skilled in the art. Devices 50 are arranged to facilitate operator control, adjustment, and result evaluation; and can be arranged along with other components of system 20 to provide and integral spectroscopy station. Subsystem 30 can also include appropriate oscillators, regulators, amplifiers, modulators, power sources, signal conditioners, format converters, and/or other components to operate in accordance with the teachings of the present invention (not shown).

In one experimental arrangement, system 20 included a QCL laser with a nominal wavelength of 8.2 micrometers (wavenumber 1219 $cm^{-1}$) with a corresponding optical frequency of about 37 TeraHertz (THz). This wavelength range corresponds to absorption features of water vapor and nitrous oxide included in the atmosphere. The wavelength scan range is about 1.5 $cm^{-1}$ (about 0.01 micrometer at 8.2 micrometers) with a sweep rate of about 400 Hertz (Hz). The frequency modulation imposed by reference/control 34 is about 200 kiloHertz (kHz) and the modulation index is less than or equal to about 0.2 $cm^{-1}$. Accordingly, about 500 full cycles of modulation result over each wavelength sweep. A telescope with about a ten inch diameter and a focal length of f3 was used to gather returned light and to direct it to an MCT form of detector. In one experiment, the distance the light beam traveled was about 40 meters (m) with the source and detector being arranged side-by-side in a common unit (a monostatic configuration). For this arrangement, the light returned to the detector was by reflection from one or more objects illuminated by the source light. These one or more objects could include the side of a building or other target(s) of opportunity. A monostatic arrangement with the source and detector close to one another in predetermined spatial relationship (such as in a common unit) readily facilitates retargeting of objects for interrogation with the system.

A bistatic configuration has also been tested that includes a reflector to generally reverse direction of laser light beam L at about the halfway point relative to the total distance D traveled. For this bistatic configuration, several different experimental distances D were tested from 0.2 kilometer (km) to 5 km; where each distance D was the length traveled by laser light beam L accumulated from source 26 to the reflector and from the reflector to detector 28. In addition, an experimental perimeter configuration with multiple reflectors to direct laser light beam L along a selected perimeter path has been tested. For these reflector-based arrangements, system 20 can again be arranged as an integral unit with the source and detector close to each other and in a predefined spatial relationship relative to one another. Nonetheless, it should be understood that in other embodiments, a region for interrogation with system 20 is positioned between the source 26 and detector 28 as depicted, for example in FIG. 1, without dependence upon reflection of the source light.

Figure 2:
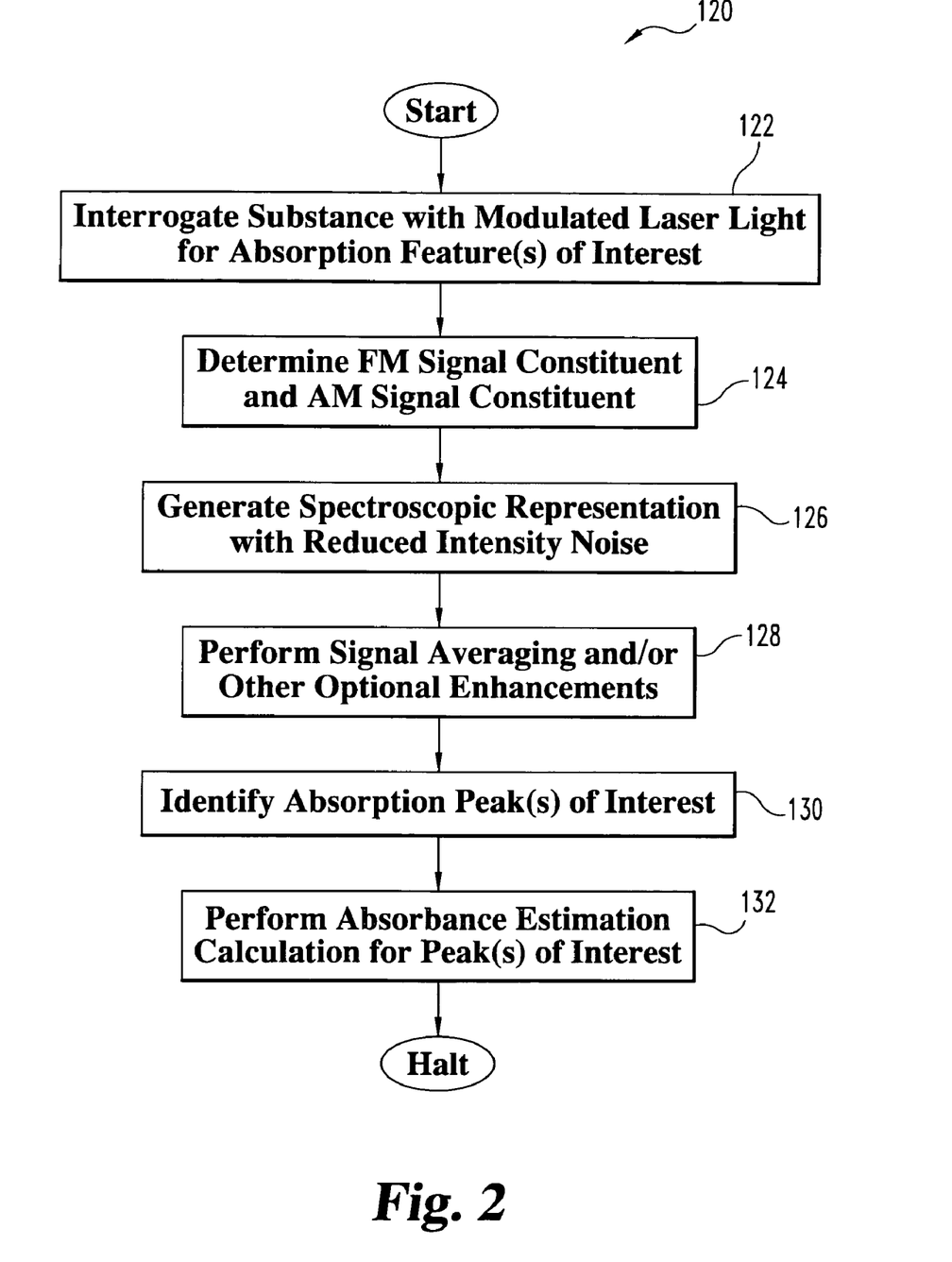
FIG. 2 is a flowchart depicting a spectroscopic evaluation procedure implemented with the system of FIG. 1.

FIG. 2 depicts spectroscopic evaluation procedure 120 in flowchart form. Procedure 120 can be implemented with system 20. Signal and data processing associated with procedure 120 can be at least partially executed in accordance with operation logic of subsystem 30. Procedure 120 starts with operation 122 in which substance S is interrogated with laser light beam L. Laser light beam L is generated with a wavelength range, sweep rate, and frequency modulation selected to detect one or more absorption features of interest. From operation 122, procedure 120 continues with operation 124.

Figure 3:
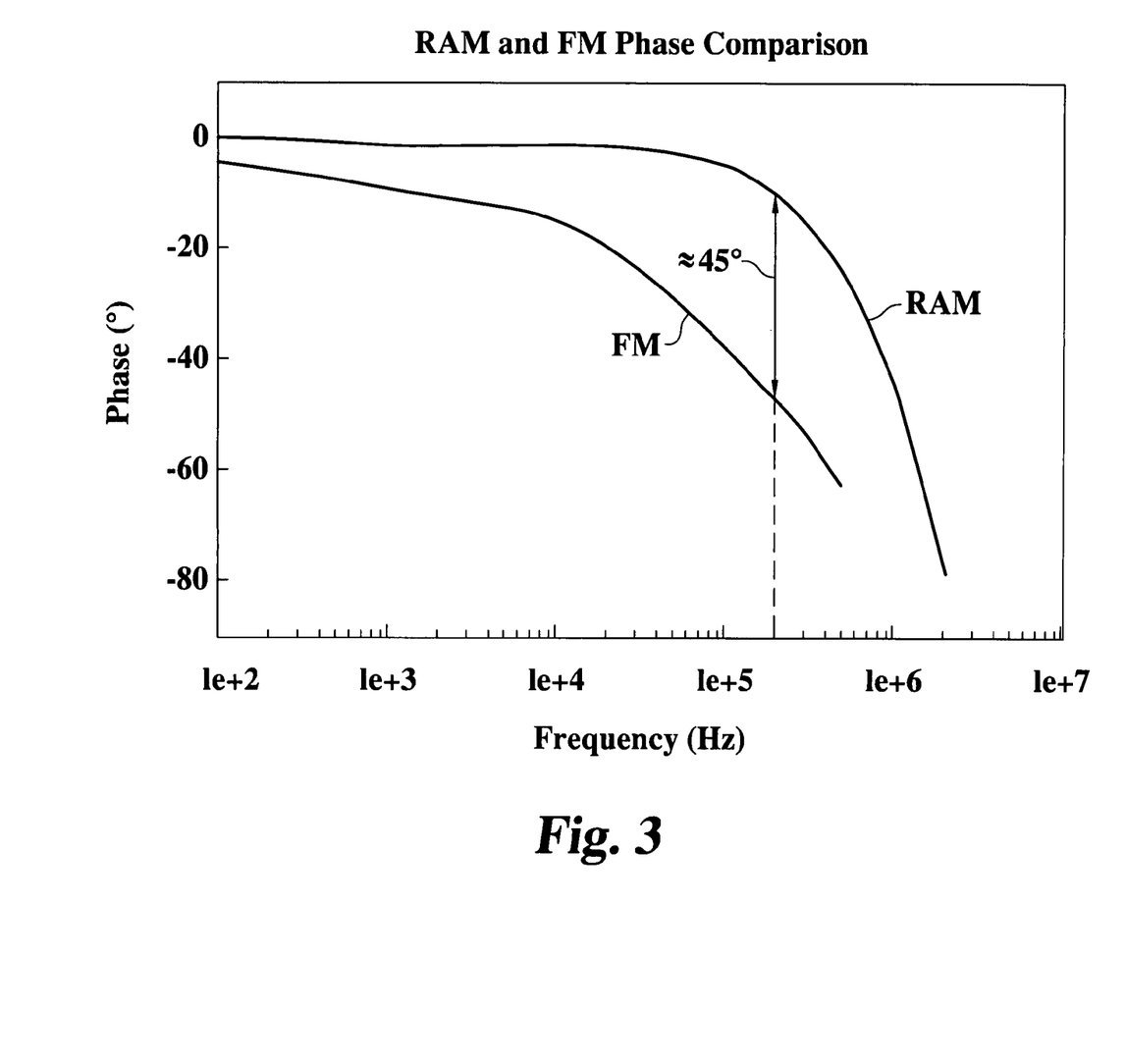
FIG. 3 is a graph depicting phase difference between FM and RAM signal constituents with respect to modulation frequency.
Figure 4:
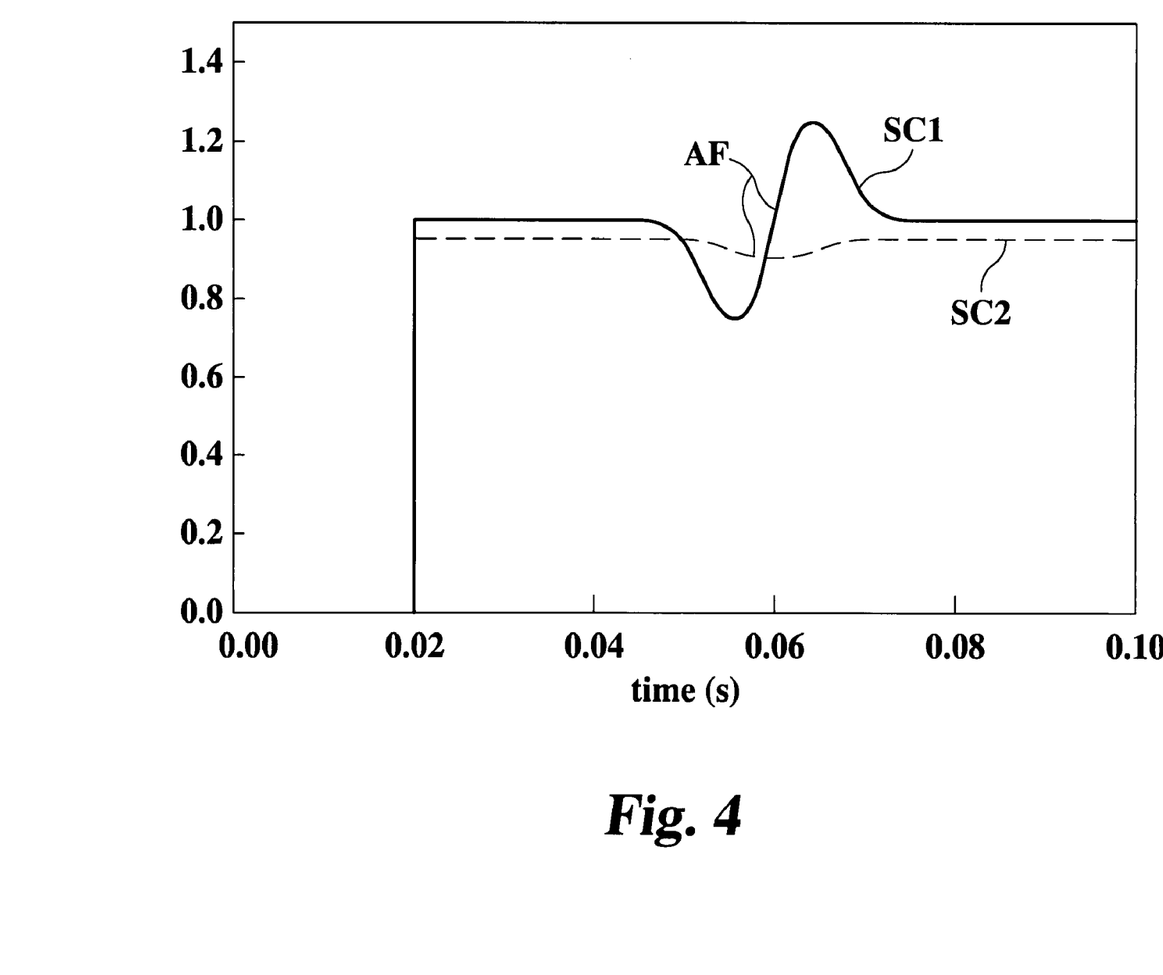
FIG. 4 is a graph comparing in-phase FM and RAM signal constituents relative to an absorption feature for an FM-optimized condition.

As previously described, frequency modulation of laser light beam L typically results in an inherent amount of amplitude modulation (RAM). For the experimental set-up previously described, it was found that the frequency modulation and amplitude modulation signal constituents are generally in-phase for lower modulation frequencies; however, at higher frequencies, the frequency modulation gradually lags behind the amplitude modulation. For 200 kHz frequency modulation, this lag is about forty-five degrees (45°) for an application using a type of quantum cascade laser for source 26. FIG. 3 depicts the change in phase difference for a frequency modulation trace (designated FM) and a residual amplitude modulation trace (designated RAM) with respect to modulation frequency for the experimental set-up, and specifically indicates the approximate 45° phase lag of the frequency modulation. Accordingly, with lock-in circuitry 36 synchronized to the frequency modulation sinusoidal waveform from reference/control 34, a primary output provides the frequency modulation signal combined with a portion of about $2^{-1/2}$ (approximately 0.707) of the amplitude modulation for a 45 degree phase difference. A solid line trace for the frequency-modulated signal constituent SC1 and a broken line trace for the amplitude-modulated signal constituent SC2 are illustrated in FIG. 4 with respect to an absorption feature AF shown in each trace. With this arrangement, the quadrature output of lock-in circuitry 36 provides an amplitude-modulated signal at the approximate 0.707 level without any frequency modulation signal portion (not shown in FIG. 4). This orthogonal quadrature output provides a convenient way to separately determine FM and AM signal constituents in operation 124. In other arrangements, different techniques can be used to determine FM and RAM signal constituents as would occur to those skilled in the art.

Figure 5:
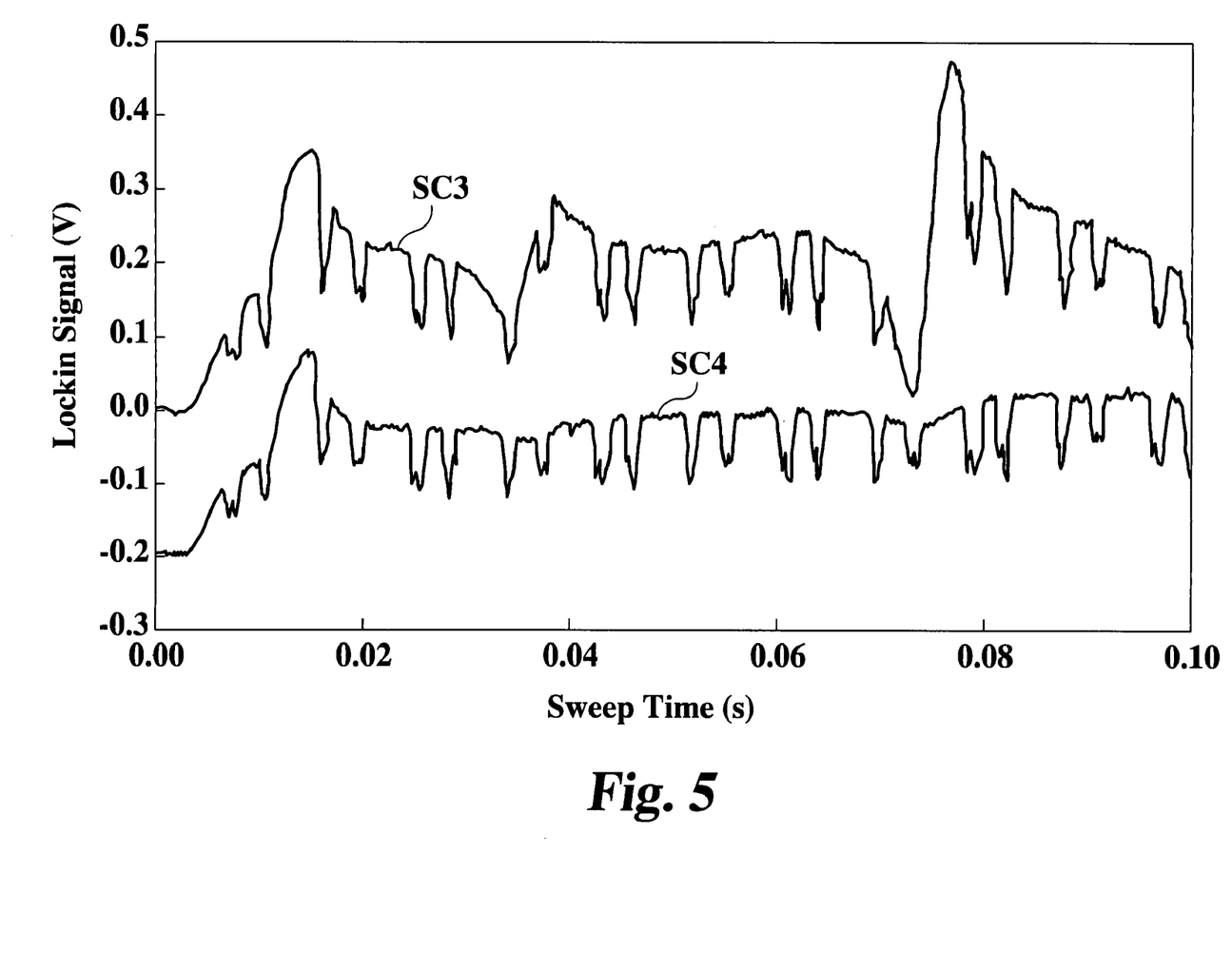
FIG. 5 is a graph showing simulated intensity noise in FM and RAM signal constituents that are 90 degrees out of phase with one another.
Figure 6:
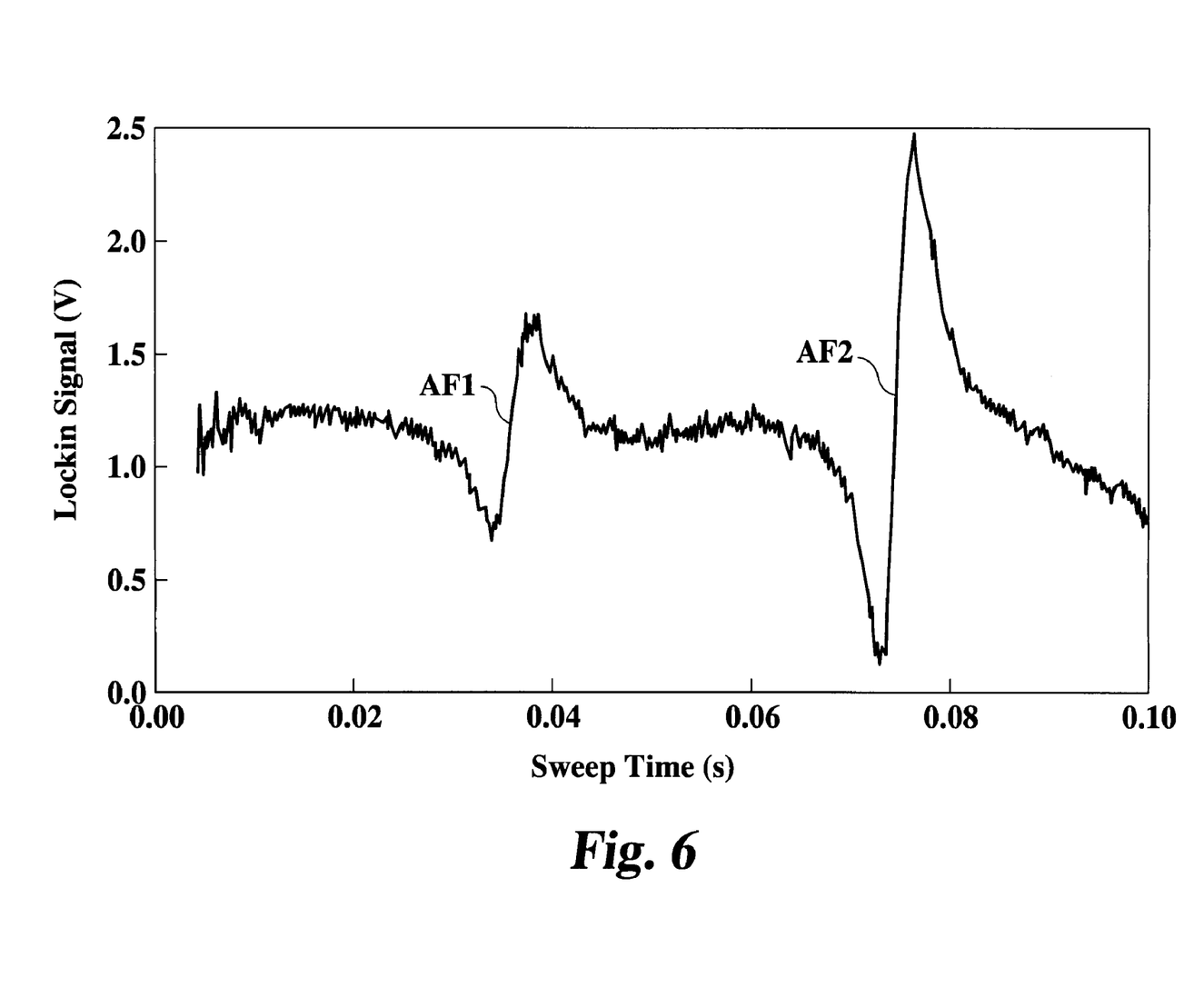
FIG. 6 is a graph of a spectroscopic signal trace based on the signal constituents of FIG. 5 with the simulated intensity noise reduced.
Figure 7:
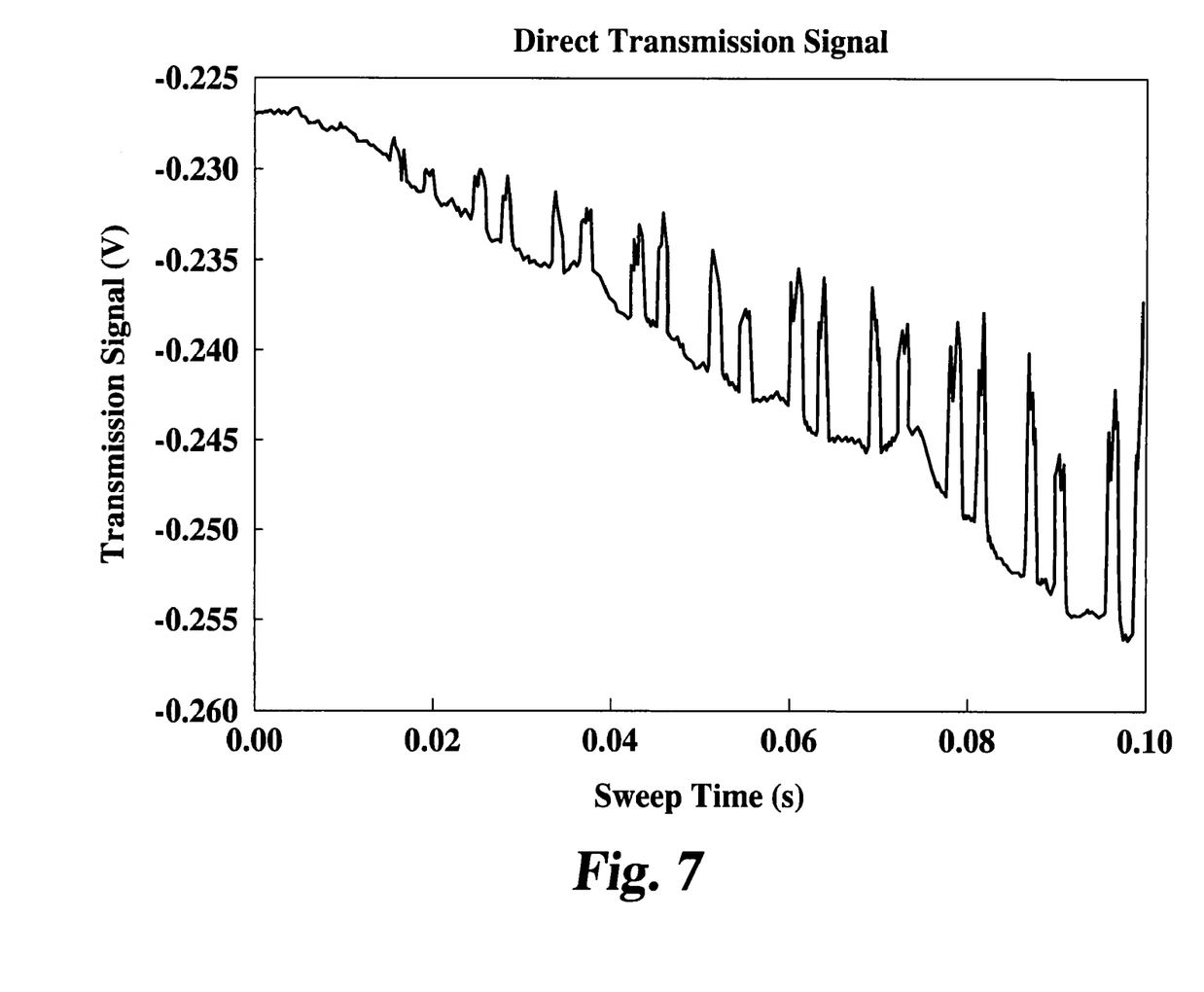
FIG. 7 is a graph showing a trace of direct absorption corresponding to the signal constituents of FIG. 5.

From operation 124, procedure 120 continues with operation 126. In operation 126, a spectroscopic representation is generated as the ratio of the FM signal constituent to the AM signal constituent. This ratio approach has been found to at least partially cancel intensity noise from atmospheric turbulence, component vibration, and the like. To demonstrate this result, a signal chopper was placed in the path of the laser light beam L to introduce an intensity noise under controlled conditions. The resulting "choppy" FM and AM signals are shown as signals SC3 and SC4, respectively in FIG. 5. Taking the ratio to reduce the chopper noise, the spectroscopic trace of FIG. 6 results. In FIG. 6, two absorption features, AF1 and AF2 are observed at about 0.038 second (s) and 0.075 s corresponding to nitrous oxide in the atmosphere. The corresponding direct absorption signal is shown in FIG. 7 for comparison with the same features AF1 and AF2 designated.

Figure 8:
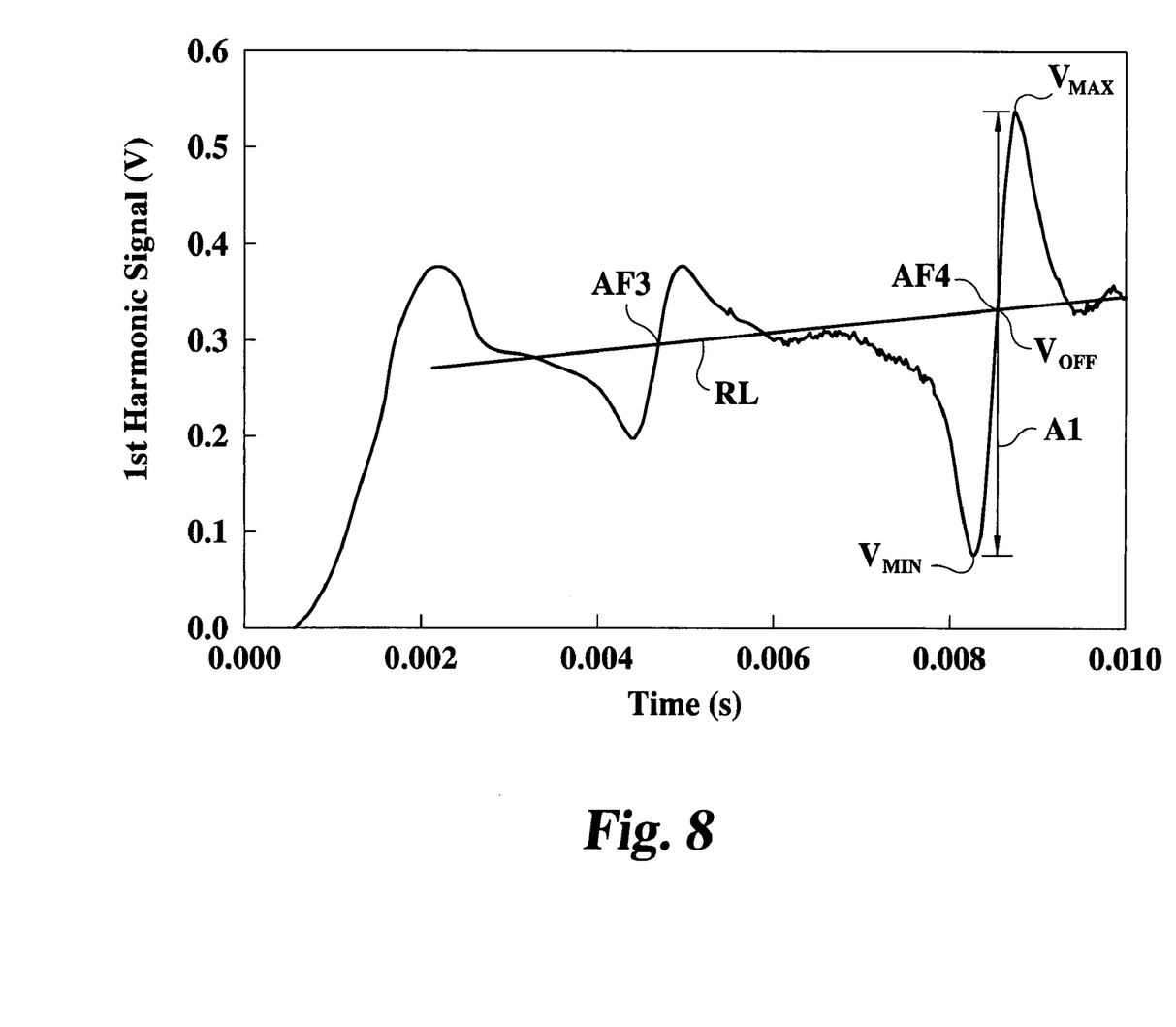
FIG. 8 is a graph to illustrate various aspects of absorbance estimation.

From operation 126, further signal processing can be executed as desired in operation 128. Such additional processing can include signal averaging or the like to improve integrity of the resulting spectroscopic information. From operation 128, procedure 120 proceeds to operation 130. In operation 130, any absorption peak of interest is identified. Referring additionally to FIG. 8, a first harmonic FM representation is shown that designates derivative absorption features AF3 and AF4. More specifically, the spectroscopic graph of FIG. 8 is based on an average of 512 traces of nitrous oxide interrogation that has absorption feature AF3 at about 0.0045 s and absorption feature AF4 at about 0.0085 s. Furthermore, the absolute magnitude of feature AF3 is depicted with the vertically-oriented double-headed arrow designated A1. Also illustrated is an estimation of the corresponding residual amplitude modulation (RAM) level as a generally straight line segment designated RL.

In operation 132, an absorbance estimate is calculated for any absorption peaks identified in operation 130. Generally, absorbance A for a given peak can be expressed as follows in expression (1):

$$A = -\ln\left(\frac{I - \Delta I}{I}\right); \quad (1)$$

where: I is the incident power and $\Delta I$ is the absorbed power. Absorbance is frequently of interest because it is directly proportional to the concentration of the substance indicated. Unfortunately, for some applications it is difficult to measure both I and $\Delta I$ to the degree desired. Because FM signals are of a derivative type, a Direct Current (DC) return signal is not often measured directly. However, the observed RAM level has been found to be directly proportional to the DC return power for certain types of lasers, such as a QCL variety for which the power curve is approximately linear (sometimes called the slope efficiency). As a result, the observed RAM level can be used to approximate I and the absolute magnitude can be used to approximate $\Delta I$. Based on this approach, the following expression (2) provides an absorbance estimator:

$$A = \frac{1}{h}\left(\frac{I_m}{I_0 - I_T}\right)\left(\frac{V_{MAX} - V_{MIN}}{2V_{OFF}}\right); \quad (2)$$

where: h is a constant dependent on a particular modulation pattern, $I_m$ is the zero-to-peak laser current modulation, $I_0$ is laser current at the peak position, $I_T$ is the laser threshold current, $V_{MAX}$ is the maximum voltage of the absorption peak, $V_{MIN}$ is the minimum voltage of the absorption peak, and $V_{OFF}$ is the RAM level value where intersected by the derivative peak line between the maximum and minimum voltages of the peak. These voltages are labeled in the FIG. 8 example. Based on testing with a known amount of gas, this form of absorbance estimation has been found to be accurate to within two percent (2%). It should be appreciated that the relationship of expression (2) applies in the situation where the phase difference (phase shift) is about 45 degrees. Generally, $V_{OFF}$ is expected to change with the degree of phase shift such that the value of the constant h may need to change to retain a desired level of accuracy for phase shifts that are not approximately 45 degrees. Such adjustments for different phase shifts can be determined empirically and/or theoretically using standard techniques known to those skilled in the field.

As a variation of operation 132, the resulting absorption peak can be of the type determined as a ratio of the FM signal constituent to the AM signal constituent per operation 126. This approach normalizes the trace with respect to the RAM level so that an estimate of absorbance based on it can be calculated in accordance with expression (2). It should be understood that for either approach, the estimation is being performed as a function that depends on RAM level. After operation 132, procedure 120 halts.

It should be appreciated that the noise reduction and absorbance estimation techniques of the present invention can each be practiced without the other. With respect to noise reduction, it is envisioned that different functions dependent on FM and AM signal constituents can be utilized to reduce noise in addition to or as an alternative to a ratio. By way of nonlimiting example, a relative comparison between such constituents can depend on difference between the FM and AM signal constituents. Generally, it should be understood that noise reduction according to the present invention can be broadly considered to include a function dependent or based on FM and AM signal constituents. With respect to absorbance estimation in particular, it should be understood that the estimator can be broadly considered to include a function dependent or based on RAM, and that a value corresponding to absorbance includes values of interest that are directly proportional to absorbance, such as concentration, for example.

Furthermore, the teachings of the present invention can be utilized in a number of different modulation approaches, including laboratory as well as remote sensing systems indoors or outdoors. In one alternative, region 24 includes an optical cavity to reflect laser light beam L back and forth between at least two reflectors a number of times with the interrogated substance positioned therebetween, and/or a ring operable to circulate laser light beam L with the interrogated substance located in the light pathway. As used herein, "frequency modulation" and "frequency-modulated" include modulation techniques that vary by phase shift on the order of 360° ($2\pi$ radians) or less (sometimes called phase modulation) as well as those resulting in frequency changes or phase changes of 360° ($2\pi$ radians) or more. Further, it is envisioned that the techniques of the present invention could be applied to frequency-modulated electromagnetic radiation with a wavelength outside the spectral range traditionally considered to define light (infrared, visible, ultraviolet), such as x-rays, to name one nonlimiting example.

Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:
1. A method, comprising:
 transmitting a modulated laser beam to a substance;
 receiving modulated laser light from the substance;
 determining an FM signal constituent and an AM signal constituent of the modulated laser light each having a degree of intensity noise; and
 reducing the intensity noise in a spectroscopic signal for the substance as a function of the FM signal constituent and the AM signal constituent.

2. The method of claim 1, wherein the function corresponds to a relative comparison between the FM signal constituent and the AM signal constituent.

3. The method of claim 2, wherein the relative comparison is in the form of a ratio between the FM signal constituent and the AM signal constituent.

4. The method of claim 1, wherein said receiving includes detecting the modulated laser beam after traveling a distance of at least 25 meters through a spectroscopic evaluation region including the substance.

5. The method of claim 4, wherein the distance is at least 1 kilometer and the evaluation region is disposed along an expanse of the atmosphere outdoors.

6. The method of claim 5, wherein the intensity noise is at least partially caused by atmospheric turbulence.

7. The method of claim 1, which includes estimating absorbance based on a frequency modulation representation of an absorption peak from the spectroscopic signal and corresponding electrical current from a laser providing the modulated laser beam.

8. A method, comprising:
 transmitting a modulated laser beam to a substance;
 detecting frequency-modulated light from the substance;
 evaluating the frequency-modulated light to identify a spectral absorption peak of the substance;
 determining a level of residual amplitude modulation of the frequency-modulated light corresponding to the absorption peak; and
 calculating a value corresponding to absorbance of the substance as a function of the level of residual amplitude modulation.

9. The method of claim 8, wherein the function further depends on one or more parameters of a frequency modulated signal characterization of the absorption peak.

10. The method of claim 9, wherein the parameters correspond to a minimum and a maximum of the absorption peak.

11. The method of claim of 10, wherein said transmitting is performed with a current-controlled laser and the function depends on one or more electrical current values for the laser.

12. The method of claim 11, wherein the parameters and the level of residual amplitude modulation correspond to voltage.

13. The method of claim 8, which includes reducing signal noise by determining the absorption peak based on a ratio between an FM constituent and a RAM constituent, and wherein the dependency of the function of the level of residual amplitude modulation is provided through the ratio.

14. A system, comprising:
 a modulated laser light source to transmit an interrogation light beam to a spectroscopic evaluation region including a substance;
 a detector responsive to modulated light from the region to provide a corresponding modulated signal; and
 a signal processing subsystem responsive to the modulated signal to generate a spectroscopic representation of the substance with light intensity noise reduced as a function of a frequency modulation constituent and a residual amplitude modulation constituent of the modulated signal.

15. The system of claim 14, wherein the modulated laser light source is operable to impart frequency modulation and residual amplitude modulation to the interrogation light beam.

16. The system of claim 14, wherein the region spans a distance of at least 1 kilometer traveled by the interrogation light beam.

17. The system of claim 14, wherein the modulated laser light source is at least one of a quantum cascade laser type and an infrared diode laser type.

18. The system of claim 14, wherein the spectroscopic representation defines an absorption peak in a derivative form and the signal processing subsystem is further operable to estimate a value corresponding to absorbance as a function of a minimum and a maximum of the absorption peak.

19. The system of claim 14, wherein the function includes a ratio between the frequency modulation constituent and the residual amplitude modulation constituent of the modulated signal.

20. A system, comprising:
a modulated laser light source to transmit an interrogation light beam to a spectroscopic evaluation region including a substance;
a detector responsive to modulated light from the region to provide a corresponding modulated signal; and
a signal processing subsystem responsive to the modulated signal to generate a spectroscopic absorption peak representation of a derivative form and calculate a value corresponding to absorbance based on magnitude of the absorption peak and a residual amplitude modulation level corresponding to the absorption peak.

21. The system of claim 20, wherein the signal processing subsystem is further operable to determine the value as a function of a minimum value and a maximum value for the peak.

22. The system of claim 21, wherein the modulated laser light source includes a current-controlled laser and the function further depends on one or more electrical current levels corresponding to the laser.

23. The system of claim 21, wherein the residual amplitude modulation level is provided in the form of a ratio between a frequency modulation signal constituent and a residual amplitude modulation signal constituent of the modulated signal.

24. The system of claim 21, wherein the region spans a distance of at least 1 kilometer traveled by the interrogation light beam.

25. The system of claim 21, wherein the modulated laser light source is at least one of a quantum cascade laser type and an infrared diode laser type.

26. The system of claim 21, wherein the spectroscopic absorption peak representation is generated by the signal processing subsystem as a function of a difference between a FM signal constituent and a residual AM signal constituent of the modulated signal to reduce intensity noise.

27. A system, comprising:
means for generating a frequency-modulated light beam with a laser;
means for detecting modulated light from a substance interrogated with the generating means;
means for reducing signal noise as a function of an FM constituent and an AM constituent of the modulated light; and
means for evaluating a characteristic corresponding to absorbance of the substance relative to an absorption peak represented in derivative form.

* * * * *